(12) United States Patent
Jeanne

(10) Patent No.: US 11,071,372 B2
(45) Date of Patent: Jul. 27, 2021

(54) SYSTEM AND METHOD FOR DETECTING MOVEMENT OF A USER OF AN ORAL HEALTH CARE DEVICE AND PROVIDING FEEDBACK

(71) Applicant: KONINKLIJKE PHILIPS N.V., Eindhoven (NL)

(72) Inventor: Vincent Jeanne, Migne Auxances (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/093,190

(22) PCT Filed: Apr. 7, 2017

(86) PCT No.: PCT/EP2017/058405
§ 371 (c)(1),
(2) Date: Oct. 12, 2018

(87) PCT Pub. No.: WO2017/178375
PCT Pub. Date: Oct. 19, 2017

(65) Prior Publication Data
US 2019/0059571 A1    Feb. 28, 2019

Related U.S. Application Data

(60) Provisional application No. 62/323,108, filed on Apr. 15, 2016.

(51) Int. Cl.
*A46B 15/00*    (2006.01)
*G16H 20/30*    (2018.01)
*G16H 30/40*    (2018.01)

(52) U.S. Cl.
CPC ...... *A46B 15/0006* (2013.01); *A46B 15/0004* (2013.01); *A46B 15/0038* (2013.01);
(Continued)

(58) Field of Classification Search
CPC ............ A46B 15/0006; A46B 15/0004; A46B 15/0038; A46B 15/0008; A46B 2200/1066; G06F 19/3481
See application file for complete search history.

(56) References Cited

U.S. PATENT DOCUMENTS 6,536,068 B1 *  3/2003  Yang .................. A46B 15/0002
                                                            15/105
9,757,065 B1 *  9/2017  Suri ..................... A61B 5/4833
(Continued)

FOREIGN PATENT DOCUMENTS

WO    2010059484 A1    5/2010
WO    2010129755 A1    11/2010
(Continued)

*Primary Examiner* — Adnan Aziz

(57) ABSTRACT

A method and system for reducing distraction of a user (10) of an oral health care device (102), includes: a sensor (112) configured to determine positions of the user during use of the oral health care device; a processor (150) in communication with the sensor and configured to calculate differences between the determined positions and to determine if the differences reach or exceed a threshold value for notifying the user; and a user interface (114) in communication with the processor and configured to alter from a normal state in an event the differences between the determined positions reach or exceed the threshold value for notifying the user.

20 Claims, 5 Drawing Sheets

(52) U.S. Cl.
CPC ............. *G16H 20/30* (2018.01); *G16H 30/40* (2018.01); *A46B 15/0008* (2013.01); *A46B 2200/1066* (2013.01)

(56) References Cited

U.S. PATENT DOCUMENTS

| | | | |
|---|---|---|---|
| 2009/0092955 A1 | 4/2009 | Hwang | |
| 2009/0215015 A1* | 8/2009 | Chu | G09B 19/0084 434/238 |
| 2009/0320227 A1* | 12/2009 | Cohen | G04F 1/005 15/167.1 |
| 2010/0170052 A1 | 7/2010 | Ortins et al. | |
| 2010/0323337 A1* | 12/2010 | Ikkink | A46B 15/0002 434/263 |
| 2012/0190505 A1 | 7/2012 | Shavit | |
| 2015/0193134 A1* | 7/2015 | Hong | G06F 3/04847 715/781 |
| 2016/0022393 A1* | 1/2016 | Yoshida | A61C 17/221 15/22.1 |
| 2016/0027467 A1 | 1/2016 | Proud | |
| 2016/0198129 A1* | 7/2016 | Proud | H04N 7/183 348/143 |
| 2016/0235357 A1* | 8/2016 | Ohmer | A46B 15/0006 |
| 2016/0292988 A1* | 10/2016 | McCleary | G08B 21/0453 |
| 2017/0238692 A1 | 8/2017 | Sarubbo | |
| 2018/0368567 A1* | 12/2018 | Buil | A46B 15/0036 |

FOREIGN PATENT DOCUMENTS

| | | |
|---|---|---|
| WO | 2010134050 A1 | 11/2010 |
| WO | 2014202250 A1 | 12/2014 |
| WO | 2014202438 A1 | 12/2014 |

* cited by examiner

SYSTEM AND METHOD FOR DETECTING MOVEMENT OF A USER OF AN ORAL HEALTH CARE DEVICE AND PROVIDING FEEDBACK

CROSS-REFERENCE TO PRIOR APPLICATIONS

This application is the U.S. National Phase application under 35 U.S.C. § 371 of International Application No. PCT/EP2017/058405, filed on Apr. 7, 2017, which claims the benefit of U.S. Provisional Patent Application No. 62/323,108, filed on Apr. 15, 2016. These applications are hereby incorporated by reference herein.

FIELD OF THE INVENTION

The present disclosure relates generally to systems and methods for detecting the movement of a user during use of an oral health care device and providing feedback to the user when the user's movement reaches or exceeds a threshold value.

BACKGROUND

Various conventional forms of tracking location of an oral health care device within a user's mouth are known. Tracking the location of the oral health care device allows for effective feedback to a user with respect to the user's oral hygiene practices. For example, if the location of a brush head is tracked within the user's mouth, portions of a group of teeth, a specific tooth, or gum section not yet cleaned may be identified so that the user can focus on those areas. Further, appropriate feedback regarding a user's technique, e.g., brushing too hard, too soft, or not long enough on a particular section of the mouth, can be provided based on implementing this conventional technology.

However, conventional tracking and feedback technology does not track the location and movement of a user, including the location and movement of a user's head, relative to and/or separate and apart from the location of the oral health care device within the user's mouth. Indeed, the conventional technology is premised on certain assumptions, e.g., that the user's head is straight, level and stationary. These limitations of the conventional technology can lead to inaccurate or less than ideal feedback and instructions/suggestions from the conventional technology to the user. Compliance with such feedback by the user can result in less than favorable oral hygiene results.

Accordingly, there is a need in the art for systems and methods for detecting the movement of a user during use of an oral health care device and providing useful feedback to enhance user compliance and improve a user's brushing behavior and/or oral hygiene.

SUMMARY OF THE INVENTION

The present disclosure is directed to inventive systems and methods for detecting the movement of a user during use of an oral health care device and providing feedback to the user when the user's movement reaches or exceeds a threshold value. Various embodiments and implementations herein are directed to a system that includes a location, position and/or movement compliance sensor that can be configured or programmed to detect movement of a user during use of an oral health care device. The sensor can be connected (wirelessly or non-wirelessly) to a controller, including a processor and a non-transitory storage medium for storing program code, which can be programmed to perform a compliance check by comparing the sensed amount (quantity or quality) of movement with a threshold value/amount (quantity or quality) of movement and to determine whether the sensed amount of movement reaches or exceeds the threshold value/amount. The controller can be further programmed to notify the user in the event the user's movement reaches or exceeds the threshold value/amount by altering/modifying a user interface (which can be located on or can be separate from the oral health care device including on any computing device or smart mirror, for example) from a normal state or otherwise providing a particular visual indication to the user. Alternatively, the indication can be audible or vibratory.

In some embodiments, the sensor can be located outside of the oral health care device and be embedded in a digital medium. For example, such a sensor can be embedded in or otherwise communicatively connected to a mobile or other computing device, including a processor and a non-transitory storage medium for storing program code, such as a smart phone or a tablet (as should be appreciated and understood by a person of skill in the art in conjunction with a review of this disclosure). Further, such a sensor can include digital camera, or a 2D, 3D, visible, IR, UV or other image sensor (as should be appreciated and understood by a person of skill in the art in conjunction with a review of this disclosure) configured and/or programmed to detect or otherwise capture the movement of a user. According to another embodiment, the sensor can be embedded in the oral health care device. Such a sensor can include an accelerometer, a gyroscope, GPS or other location, positioning and/or movement sensor (as should be appreciated and understood by a person of skill in the art in conjunction with a review of this disclosure).

Generally, in one aspect, a method for reducing distraction of a user of an oral health care device, includes the steps of: detecting movement of the user during use of the oral health care device; determining whether an amount of the movement reaches or exceeds a threshold value for notifying the user of the movement; and in an event the movement reaches or exceeds the threshold value, notifying the user of the movement by altering a user interface from a normal state.

According to an embodiment, the step of detecting movement of the user includes capturing 2D or 3D images.

According to an embodiment, the step of detecting movement of the user includes using an accelerometer or a gyroscope positioned within the oral health care device According to an embodiment, the step of detecting movement of the user includes capturing images of the user using a camera.

According to an embodiment, the step of determining whether the amount of the movement reaches or exceeds the threshold value includes extracting sets of visual features including positions of facial components of the user from the captured images, calculating differences between the sets of visual features, and comparing the differences to predefined values.

According to an embodiment, the step of determining whether the amount of the movement reaches or exceeds the threshold value includes extracting sets of linear or non-linear features from captured sensor data, calculating differences between the sets of linear or non-linear features, and comparing the differences to predefined values.

According to an embodiment, the step of determining whether the amount of the movement reaches or exceeds the threshold value includes calculating a weighted distance between the differences and corresponding predefined values.

According to an embodiment, the differences between the sets of visual features are distances between the positions of the facial components of the user from image to image, and the corresponding predefined values are acceptable movement distances for each facial component.

According to an embodiment, the user interface includes a visual image and wherein altering a user interface from a normal state includes blurring the image.

According to another aspect, a system for reducing distraction of a user of an oral health care device, includes: a position sensor configured to determine positions of the user during use of the oral health care device; a processor in communication with the position sensor and configured to calculate differences between the determined positions and to determine if the differences reach or exceed a threshold value for notifying the user; and a user interface in communication with the processor and configured to alter from a normal state in an event the differences between the determined positions reach or exceed the threshold value for notifying the user.

According to an embodiment, the position sensor includes a camera to capture images of the user.

According to an embodiment, the processor is configured to extract sets of visual features including positions of facial components of a user from the captured images, calculate differences between the sets of visual features, and compare the differences to predefined values.

According to an embodiment, the processor is configured to extract sets of linear or non-linear features from captured sensor data, calculate differences between the sets of linear or non-linear features, and compare the differences to predefined values.

According to an embodiment, the position sensor is an accelerometer or a gyroscope positioned within the oral health care device According to an embodiment, the processor is configured to calculate a weighted distance between the differences and corresponding predefined values.

According to an embodiment, the differences between the sets of visual features are distances between the positions of the facial components of the user from image to image, and wherein the corresponding predefined values are acceptable movement distances for each facial component.

According to an embodiment, the user interface includes a visual image and wherein the processor is configured to blur the image in an event the differences between the determined positions exceed the threshold value.

As used herein for purposes of the present disclosure, the term "controller" is used generally to describe various apparatus relating to the operation of a stream probe apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present disclosure discussed herein. The terms "program" or "computer program" are used herein in a generic sense to refer to any type of computer code (e.g., software or microcode) that can be employed to program one or more processors or controllers.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure is directed to inventive systems and methods for detecting the movement of a user during use of an oral health care device and providing feedback to the user when the user's movement reaches or exceeds a threshold value. More generally, Applicant has recognized and appreciated that it would be beneficial to track the movement of the user, separate from or in addition to the oral health care device, in order to provide more accurate feedback to the user. Various embodiments and implementations herein are directed to a system that includes a location, position and/or movement compliance sensor that can be configured or programmed to detect movement of a user during use of an oral health care device. The sensor can be located outside of the oral health care device and be embedded in a digital medium. Alternatively, the sensor can be embedded within the oral health care device itself. The sensor can be connected (wirelessly or non-wirelessly) to a controller, including a processor and a non-transitory storage medium for storing program code, which can be programmed to perform a compliance check by comparing the sensed amount (quantity or quality) of movement with a threshold value/amount (quantity or quality) of movement and to determine whether the sensed amount of movement reaches or exceeds the threshold value/amount. The controller can be further programmed to notify the user in the event the user's movement reaches or exceeds the threshold value/amount by altering/modifying a user interface (which can be located on or can be separate from the oral health care device) from a normal state or otherwise providing a particular indication (e.g., visual indication) to the user.

A particular non-limiting goal of utilization of the embodiments and implementations herein is to provide certain feedback to a user of a power toothbrush, e.g., a Philips Sonicare™ toothbrush (manufactured by Koninklijke Philips Electronics, N.V.). Such information can, for example, be related to alerts, instructions, indications or sensory result messages related to the movement of a user's body (or head in particular) beyond a predefined threshold value(s) in order to yield better use of the power toothbrush.

According to other embodiments and implementations, pertinent alerts/information/indications/messages can be provided to users of any power medical, dental, shaving, grooming, mother and child care devices (handheld and non-handheld) or other personal care devices, for example, which can incorporate and benefit from the configurations and functionalities described herein (as should be appreciated by a person of ordinary skill in the art in conjunction with a review of this disclosure).

Figure 1:
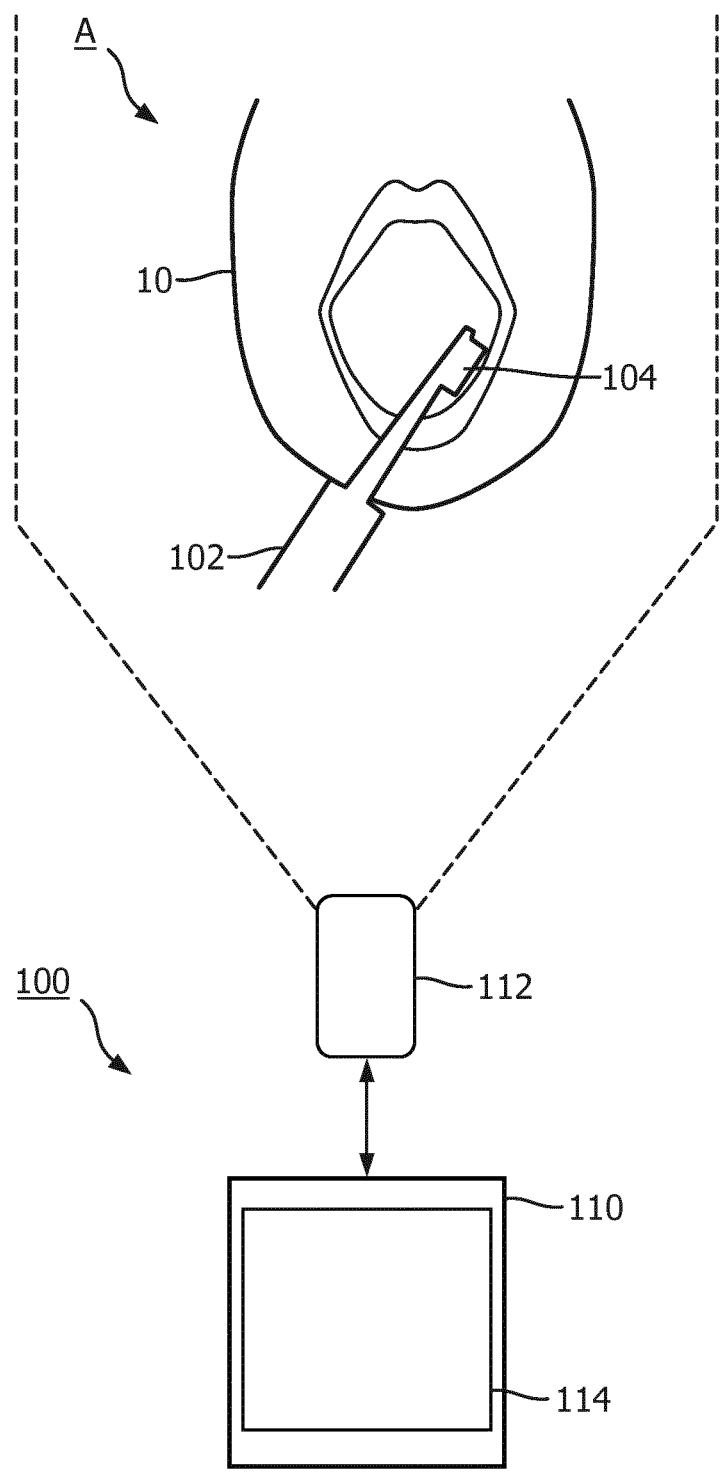
FIG. 1 is a schematic representation of a system for detecting the movement of a user during use of an oral health care device and providing feedback to the user when the user's movement reaches or exceeds a threshold value according to an embodiment.

Referring to FIG. 1, in one embodiment, is a schematic representation of a system 100 configured and/or programmed to detect the movement of a user 10 within sensor area A during use of an oral health care device 102—such as a toothbrush, oral irrigator, or other tooth or gum cleaning device—having a distal tip or head portion 104, to determine whether the user's movement reaches or exceeds a threshold value, and to provide feedback to the user when the user's movement reaches or exceeds the threshold value. System 100 may comprise a computing device 110 with one or more sensors 112 and a user interface 114. The one or more sensors 112 and a user interface 114 may each be embedded in the computing device 110 or be separate therefrom and communicatively and operably connected thereto.

According to an embodiment, computing device 110 may be a general purpose computer, a mobile device, smart phone, tablet, a custom dedicated computing device, or any other computing device capable of storing and executing the algorithm(s)/program(s) described herein. Computing device 110 may be configured and/or programmed with a face tracking algorithm/program, as should be appreciated and understood by a person of skill in the art in conjunction with a review of this disclosure. A program operated by computing device 110 may be a mobile or other application, which may also be configured to display on the user interface 114 feedback indications to a user based on analyses and determinations made by a controller 142 (see FIG. 2) implementing the program based on sensor 112 input regarding the user's movement during use of the oral health care device 102. In an embodiment where the computing device 110 is a device physically separated from and communicatively connected to another computing device running a particular application, computing device 110 may cooperate with the separate computing device running the particular application for such analysis, determination, and display. Further, computing device 110 may be associated with a user interface 114 physically separated from computing device 110 for displaying feedback indications to a user 10. For example, computing device 110 may be associated with a mirror, such as a "smart mirror," where a user could view their face while using oral care device 102. According to an embodiment, the smart mirror may comprise a display (or alternative user interface 114) behind a half-translucent mirror.

According to a further embodiment, the one or more sensors 112 can include a 2D, 3D, visible, Infrared (IR), ultraviolet (UV) or other image sensor (as should be appreciated and understood by a person of skill in the art in conjunction with a review of this disclosure), or a combination thereof, configured and/or programmed to detect or otherwise capture the movement of a user (e.g., by capturing traditional digital 2D images, or 3D images etc.). For example, sensor 112 may be a standard CMOS camera, or may be a camera embedded on a mobile device. Sensor 112 may also comprise a plurality of optical sensors. For example, one optical sensor may be configured to receive infrared light or UV light, while another is configured to view and capture a 2D or 3D image of a user's face. In an embodiment with more than one sensor 112, the plurality of sensors can be placed in a variety of positions around and focused on the user within sensor area A (as may be appropriate for a given environment and user shape, size and position within sensor area A, as should be understood by a person of ordinary skill in the art in conjunction with a review of this disclosure). If more than one sensor 112 is contemplated and used, the sensor input from each utilized sensor can be analyzed separately or as combined input by the computing device 110. Such combined input could be averaged, and/or the input from certain sensors 112 can be weighted depending on the importance of the reading of the particular sensor 112 (which can depend on positioning and angle of the sensor 112 with respect to the user 10).

Figure 2:
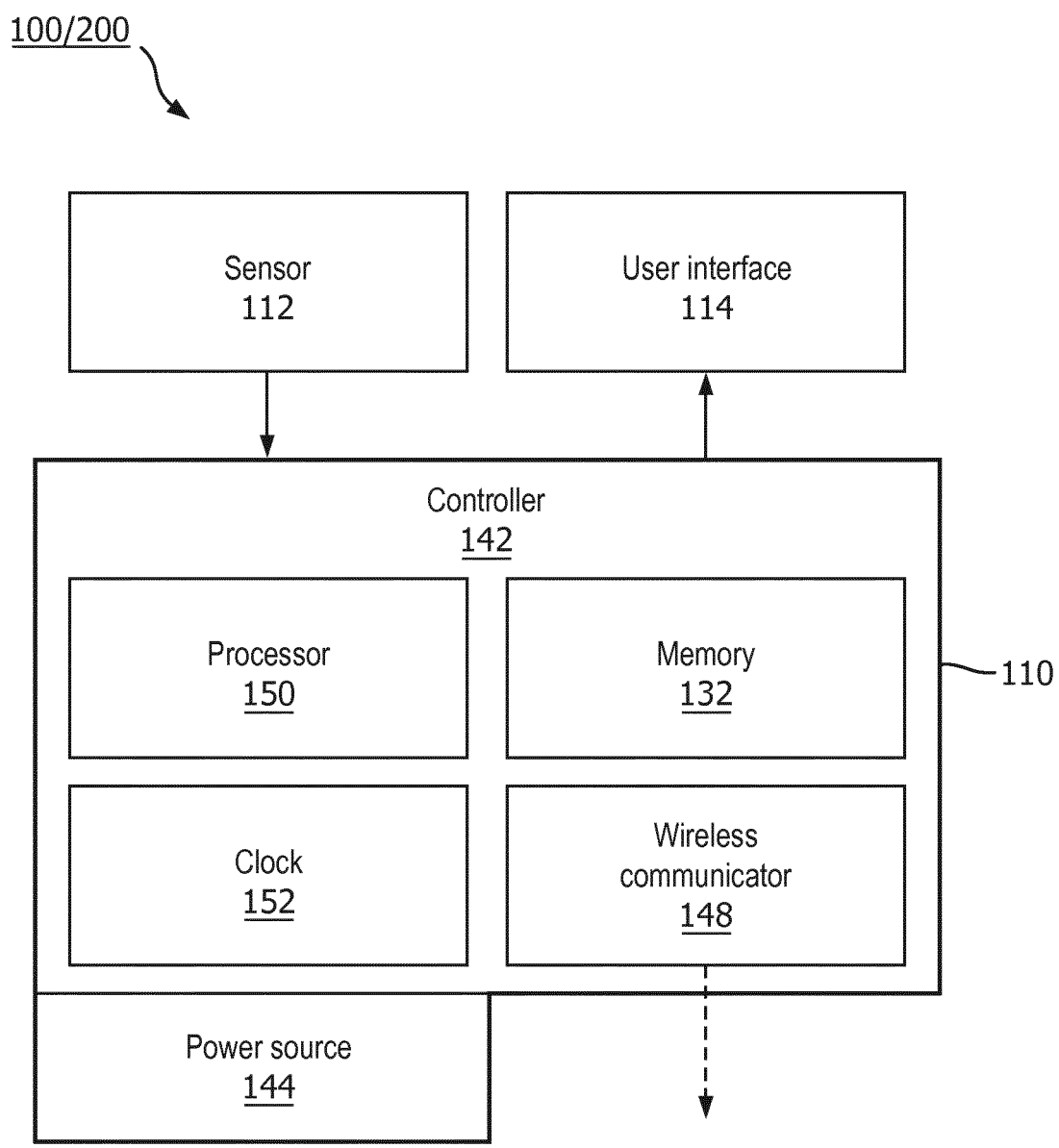
FIG. 2 is a schematic representation of the basic control components of the systems of FIG. 1 and FIG. 4 according to an embodiment.

Turning to FIG. 2, according to an embodiment, a schematic representation of the basic control components of system 100 (and system 200, as described below) is provided. As described herein, system 100 can be programmed and/or configured to detect the movement of a user within sensor area A during use of an oral health care device 102 having at distal tip or head portion 104, and to provide feedback to the user when the user's movement reaches or exceeds a threshold value. According to an embodiment, certain control components can be embedded in computing device 110 and can include a controller 142 that is programmed and/or configured to analyze information/data, transmit/receive information, data and/or commands (control signals) from/to each of the other respective components of the computing device 110 or external components/devices as may be appropriate to carry out the functions and methods described herein (as should be appreciated and understood by those of skill in the art in conjunction with a review of this disclosure). As discussed further herein, information/data that can be analyzed and/or used by the controller 142 to carry out the functions and methods described herein can be detected by and received from one or more sensors 112. In brief, the controller 142 can be programmed and/or configured to effectuate the (i) detection by a sensor 112 of the movement of a user 10 within sensor area A during use of an oral health care device 102, (ii) analysis of the detected user movement, (iii) determination of whether the user's movement reaches or exceeds a threshold value, and (iv) providing of feedback to the user at the user interface 114 when the user's movement reaches or exceeds the threshold value.

According to a further embodiment, as shown in FIG. 2, in addition to the sensor 112, user interface 114, and the controller 142, the control components of system 100 can also include, for example, a power source 144, a processor 150 and a non-transitory storage medium containing program code (to cause the processor 150 to execute an algorithm/program in accordance with the various embodiments described herein), memory 132, clock 152, and wireless communicator 148 (each of which can be part of the controller 142). Sensor 112 can be any of the sensors described or otherwise envisioned herein, and can be programmed and/or configured to obtain sensor data regarding one or more aspects of the user's movement (e.g., head movement) during a brushing session. Controller 142 can receive the sensor data from sensor 112 in real-time or periodically. For example, sensor 112 may send a constant stream of sensor data to controller 142 for storage and/or analysis, or may temporarily store and aggregate or process data prior to sending it to controller 142. Once received by the controller 142, the sensor data from the brushing session can be processed by processor 150. According to an embodiment, the processing can generally comprise of one or more of the following steps: (i) normalizing or otherwise processing the sensor data for further analysis; (ii) retrieving stored pre-programmed or user-defined user movement standards/thresholds from memory 132 (which can be inputted into the computing device 110 as should be appreciated by a person of ordinary skill in the art in conjunction with a review of this disclosure); (iii) comparing the sensor data to the retrieved standards/thresholds; (iv) determining if there are any sensor data that meet or differ sufficiently (beyond a pre-defined threshold value) from the retrieved standards; (v) determining whether the sensor data triggers an output to the user based on the stored standards; and (vi) outputting data to the user in the indication on the user interface 114 regarding the triggering sensor data. In other words, sensor data can be compared to pre-programmed standards/thresholds to determine if the display of a particular indication on the user interface 114 is warranted (e.g., straighten head out by tilting slightly to the left). Additionally, the timing of the display of a particular indication on a user interface 114 can be in real time, or periodically, with reference to clock 152 as may be appropriate.

Wireless communicator 148 can be configured and/or programmed to transmit sensor data to a wireless transceiver (not shown). For example, wireless communicator 148 may transmit sensor data via a WiFi connection over the Internet or an Intranet to a dental professional, a database, or other location. Alternatively, wireless communicator 148 may transmit sensor or feedback data via a Bluetooth or other wireless connection to a local device (e.g., a separate computing device), database, or other transceiver. For example, a wireless communicator 148 allows the user to transmit sensor data to a separate database to be saved for long-term storage, to transmit sensor data for further analysis, to transmit user feedback to a separate user interface 114, or to share data with a dental professional, among other uses. Wireless communicator 148 may also be a transceiver that can receive user input information, including the above referenced standards (as should be appreciated by a person of ordinary skill in the art in conjunction with a review of this disclosure). Other communication and control signals described herein can be effectuated by a hard wire (non-wireless) connection, or by a combination of wireless and non-wireless connections.

According to an embodiment, historically gathered data may be sensed by sensor 112, and gathered and stored in memory 132. For example, an average value per day, week, month, etc. of user movement above, below, or at a predefined threshold value can be stored with reference to clock 152. A particular indication can be displayed on the user interface 114 indicating to the user that his/her movement has improved or has become worse over time.

Figure 3:
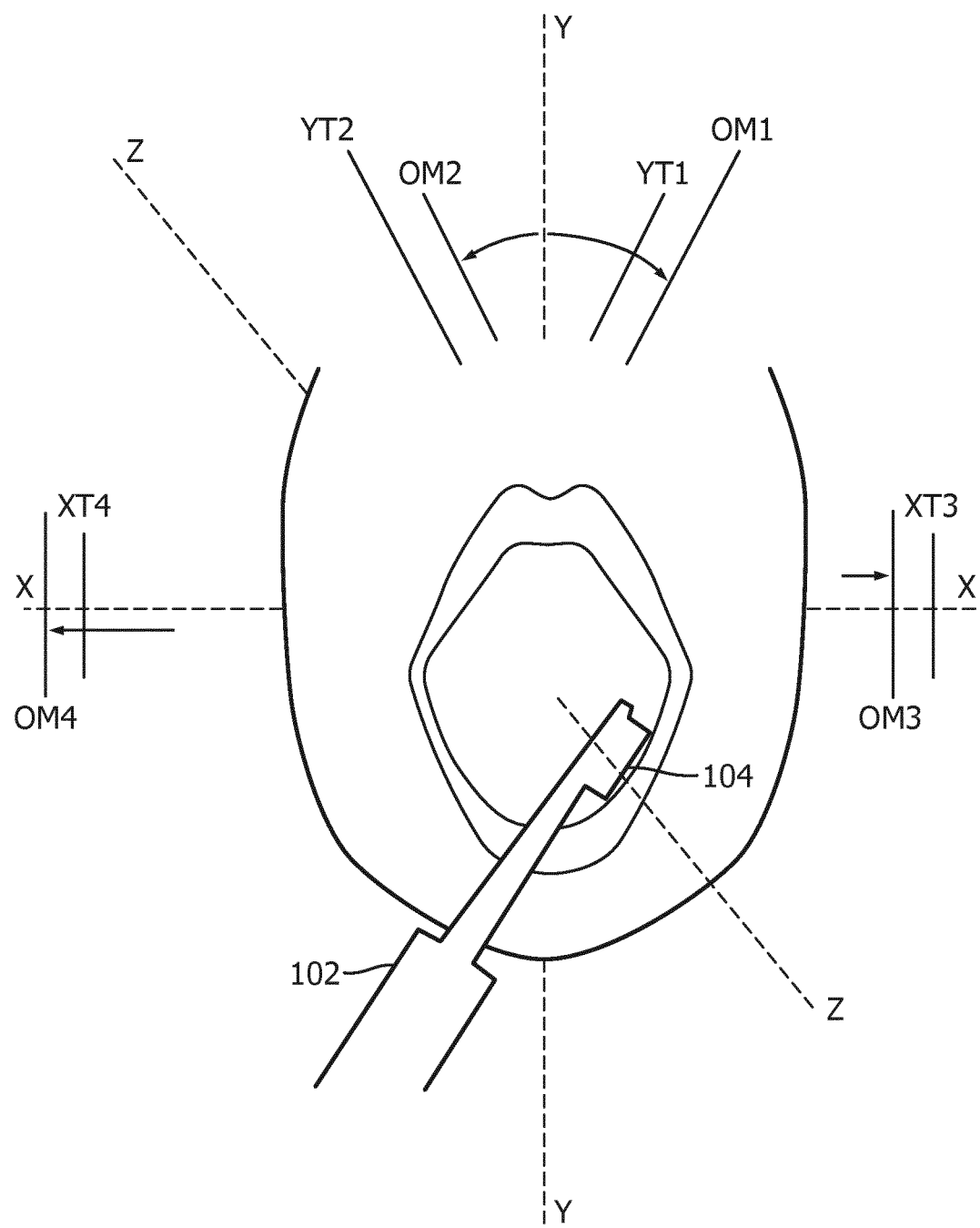
FIG. 3 is a schematic representation of a user's head during use of an oral health care device with threshold value and observed movement/position indications according to an embodiment.

Advantages of embodiments (as briefly detailed above and shown in FIGS. 1 and 2, and described below and shown in FIG. 3) is illustrated by the following exemplary use description with reference to FIG. 3. However, the particular components, uses, functionalities and amounts thereof recited in this description, as well as other conditions and details, are to be interpreted to apply broadly in the art and should not be construed to unduly restrict or limit the invention in any way.

Referring to FIG. 3, in one embodiment, a schematic representation of a user's 10 head is shown with an X-axis, a Y-axis, and a Z-axis positioned there through. Certain predefined/preprogrammed standards/thresholds ("T"), which can be stored in memory 132 and retrieved by processor 150 as appropriate, are shown along or with respect to certain axes (i.e., Y and X), and can include the following: (i) YT1—indicating a first threshold distance from the Y-axis to which the user's head can be tilted to the user's left in the direction of the positive X-axis; (ii) YT2—indicating a second threshold distance from the Y-axis to which the user's head can be tilted to the user's right in the direction of the negative X-axis; (iii) XT3—indicating a third threshold distance to which the user's head can be moved to the user's left along the positive X-axis; and (iv) XT4—indicating a fourth threshold distance to which the user's head can be moved to the user's right along the negative X-axis. Even though a plurality of threshold values are shown in FIG. 3, there can be one threshold value or more than on threshold value that can be implemented for any given brushing session.

According to an embodiment, each of the standards/thresholds shown in FIG. 3 can be measured/plotted/calculated from a first point in time, i.e., where a user's head exists and the three axes positioned therethrough at a particular point in time (the head may not be perfectly straight, but this point of the head in space can be the reference point at a time 0 nonetheless), and observed movement over a period of time from that reference point can be measured. Stated differently, this reference point can be a first point in time where the sensor obtains its first reading. The user's observed movement (change/delta in location from this reference point 0 with reference to one or more of the three axes) can be measured from this point and analyses and determinations can be made as to whether the user's movement reaches or exceeds any threshold values and as to whether an indication needs to be displayed to the user on user interface 114.

Sensor 112 of system 100 can be used to detect a user's movement from the reference point 0 over a period of time, and can communicate this data to the controller 142. The controller 142 can communicate this data to the processor 150, which can be programmed to execute various algorithm(s)/program(s) described herein including face tracking algorithm(s)/program(s). The face tracking algorithm(s)/program(s) can include an algorithmic module(s) including subcomponents for extracting specific features from data provided by the sensor 112 (e.g., a face detector subcomponent, and a sub-component for characterizing the movement of the user's face in 2D or 3D over a time period), comparing these features with one or more of the predefined standards/thresholds (e.g., a sub-component for comparing the observed movement with predefined standards/thresholds), and displaying an indication on or otherwise altering a user interface 114 from an existing state when one or more of the predefined standards/thresholds have been met or exceeded (a sub-component for providing a compliance level based on the distance between the observed features and the predefined standards/thresholds). The distance can be defined, for example, as the distance between two feature vectors as shown in two separate digital images captured by the sensor 112 and can correspond to the respective pixel values, for example, of each digital image (as should be understood by a person of ordinary skill in the art in conjunction with a review of this disclosure). This can include, for example, the distance between the feature vector of the tip of a user's nose at reference point 0 and at time 0, and the feature vector of the tip of a user's nose at point N in space at time N'. Alternatively, the distance can be defined as the distance between maximum values of measured distance of the feature vector of the tip of a user's nose during a particular time period after time 0 and from reference point 0. Additionally, such distances can be weighted based on the criticality of specific features (e.g., movement away from Y-axis is less desirable than movement along the Y-axis). The facial tracking algorithm may identify other features of the user's face, such as an outline of the user's face, the location of the user's eyes, lips, etc., each of which could be represented by a feature vector. The computing device 110 may thereafter process the signals received by sensor 112 so as to identify the location of the user at a particular time after time 0 and to assess the movement of the user beyond reference point 0.

Turning back to FIG. 3, sensor 112 detects several actual observed movements/positioning ("OM") over a period of time and communicates these observed movements/positions to the controller 142 for further analysis as set forth above. The processor 150 is programmed to determine that the observed movements include the following: (i) OM1—indicating a first observed movement where the user's head tilted to the user's left a distance in the direction of the positive X-axis and exceeded the first threshold distance YT1 at time 1; (ii) OM2—indicating a second observed movement where the user's head tilted to the user's right a distance in the direction of the negative X-axis and did not reach or exceed the second threshold distance YT2 at time 2; (iii) OM3—indicating a third observed movement where the user's head moved a distance along the positive X-axis and did not reach or exceed the third threshold distance XT3 at time 3; and (iv) OM4—indicating a fourth observed movement where the user's head moved a distance along the negative X-axis and exceeded the fourth threshold distance XT4 at time 4.

According to an embodiment, in light of these results, the processor 150 can send a control signal to the user interface 114 to provide an indication to the user (e.g., straighten head, stop moving head, bring head back to reference point 0, or blur the user interface until the user complies with a preferred position of the head or limitation of a movement of the head) when the user exceeds the first threshold distance YT1 at time 1. Alternatively, the processor 150 can send a control signal to the user interface 114 to provide an indication to the user when the user exceeds the first threshold distance YT1 and the fourth threshold distance XT4, or just the fourth threshold distance XT4 over a particular time period. Additionally, the processor 150 can send a control signal to the user interface 114 to provide an indication to the user when the user reaches or exceeds one or more threshold distances multiple times over a particular time period. According to certain embodiments, no time period limiter is contemplated. A person of ordinary skill in the art should appreciate, in conjunction with a review of this disclosure, that the processor 150 can be programmed in any number of ways to provide a control signal to the user interface to provide a particular indication to the user in view of a particular lack of compliance with any number of possible predefined threshold values.

Figure 4:
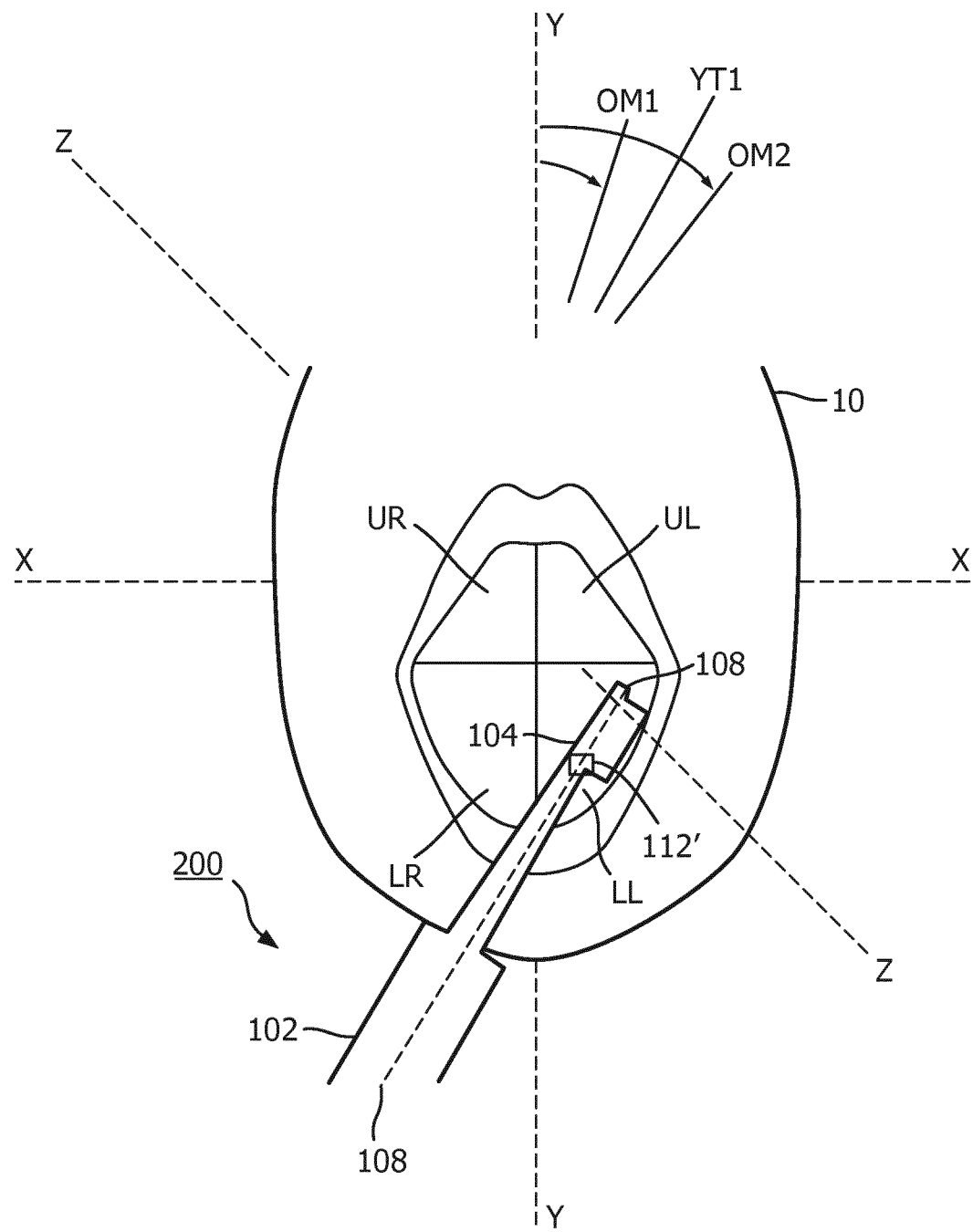
FIG. 4 is a schematic representation of a system for detecting the movement of a user during use of an oral health care device and providing feedback to the user when the user's movement reaches or exceeds a threshold value according to an alternative embodiment.

Advantages of embodiments (as briefly detailed above and shown in FIG. 2, and described below and shown in FIG. 4) is illustrated by the following exemplary use description with reference to FIG. 4. However, the particular components, uses, functionalities and amounts thereof recited in this description, as well as other conditions and details, are to be interpreted to apply broadly in the art and should not be construed to unduly restrict or limit the invention in any way.

Referring to FIG. 4, according to an alternative embodiment, a schematic representation of a system 200 configured and/or programmed to detect the movement of a user 10 during use of an oral health care device 102, determine whether the user's movement reaches or exceeds a threshold value, and to provide feedback to the user when the user's movement reaches or exceeds the threshold value is shown. As opposed to the embodiment of the sensor 112 shown in FIG. 1, a sensor 112' can be embedded in the oral health care device 102. Such a sensor 112' can include one or more of the following: an accelerometer, a gyroscope, GPS or other location, positioning and/or movement/motion sensor (as should be appreciated and understood by a person of skill in the art in conjunction with a review of this disclosure). The sensor 112' of the oral health care device can be similarly communicatively connected to a controller 142 with each of the components as shown in FIG. 2 including a processor 150, memory 132, clock 152, power source 144, wireless communicator 148 and user interface 114 (the corresponding disclosure of which is expressly incorporated by reference in its entirety herein as applied to this embodiment), which can be embedded in or separate from the oral health care device 102. Sensor 112' can be configured to detect that the user has picked up the oral health care device 102 or removed it from a cradle and is about to use the oral health care device 102 (i.e., positioned for use). For example, sensor 112' may detect motion using a variety of different motion-detecting sensors, and can send a signal to the processor 150 that the user has picked up the toothbrush and that an appropriate indication can be projected on user interface 114 as may be appropriate during a brushing event in accordance with this disclosure.

As further shown in FIG. 4, an X-axis, a Y-axis, and a Z-axis are positioned through the user's 10 head in a similar manner as shown in FIG. 3. Certain predefined/preprogrammed standards/thresholds ("T") can be stored in memory 132 and retrieved by processor 150 as appropriate, as discussed above with reference to FIG. 3. For example, the following predefined/preprogrammed standard/threshold is shown: YT1—indicating a first threshold distance from the Y-axis to which the user's head can be tilted to the user's left in the direction of the positive X-axis. Even though one threshold value is shown in FIG. 4, there can more than one threshold value that can be implemented for any given brushing session. Additionally, the following mouth segments are illustrated in FIG. 4: upper left ("UL"), lower left ("LL"), upper right ("UR") and lower right ("LR").

According to an embodiment, as discussed with respect to FIG. 3, the standard/threshold shown in FIG. 4 can be measured/plotted/calculated from a first point in time, i.e., where a user's head exists and the three axes positioned there through at a particular point in time (the head may not be perfectly straight, but this point of the head in space can be the reference point at a time 0 nonetheless), and observed movement over a period of time from that reference point can be measured. Stated differently, this reference point can be a first point in time where the sensor obtains its first reading, and the user's observed movement (change/delta in location from this reference point 0 with reference to one or more of the three axes) can be measured from this point and analyses and determinations can be made as to whether the user's movement reaches or exceeds any threshold values and as to whether an indication needs to be displayed to the user on user interface 114.

Sensor 112' can be used to detect a user's movement from the reference point 0 over a period of time, and can communicate this data to the controller 142. The controller 142 can communicate this data to the processor 150, which can be programmed to execute various algorithm(s)/program(s). The algorithm(s)/program(s) can include an algorithmic module(s) including subcomponents for extracting specific features from data provided by the sensor 112' (e.g., a sub-component for determining the location of the oral health care device 102 in a mouth segment based on sensor input), comparing these features with one or more of the predefined standards/thresholds (e.g., a sub-component comparing the observed location with predefined standards/thresholds), and displaying an indication on or otherwise altering a user interface 114 from an existing state when one or more of the predefined standards/thresholds have been met or exceeded (a sub-component providing a compliance level based on the distance between the observed features/locations and the predefined standards/thresholds).

Turning back to FIG. 4, sensor 112' detects oral health care device within the user's 10 mouth in the LL segment, and the user brushing the lower left set of teeth in the direction of the longitudinal axis 108 of the oral health care device 102 with the bristles facing down toward the lower left teeth at reference point 0 at time 0 (e.g., as detected by an accelerometer characterizing acceleration of the oral healthcare device in the direction along the longitudinal axis 108, a gyroscope indicating the bristles are facing down, and/or a GPS position sensor or other location sensor to indicate that the oral health care device 102 is within the LL segment, each of which can be part of sensor 112'). The computing device 110, as shown and described with FIGS. 1-3 above, can be used in conjunction with the embodiment shown and described with respect to FIG. 4, to assist with the sensing of the location of the user's face etc.

Sensor 112' detects a couple of actual observed movements ("OM") from reference point 0 (e.g., tilting of the user's head to the left toward the positive x-axis as could be determined by the gyroscope as the user continued to brush the bottom left set of teeth in mouth segment LL as described above and determined in part by an accelerometer and/or the other location sensors) over a period of time and communicated these observed movements to the controller 142 for further analysis as set forth above. The processor 150 is programmed to determine that the observed movements include the following: (i) OM1—indicating a first observed movement where the user's head tilted to the user's left a distance in the direction of the positive X-axis and did not reach or exceed the first threshold distance YT1 at time 1; and (ii) OM2—indicating a second observed movement where the user's head tilted to the user's left a distance in the direction of the positive X-axis and exceeded the first threshold distance YT1 at time 2.

According to an embodiment, in light of these results and similarly to FIG. 3 and the corresponding description, the processor 150 can send a control signal to the user interface 114 to provide an indication to the user (e.g., straighten head, stop moving head, bring head back to reference point 0, or blur the user interface until the user complies with a preferred position of the head or limitation of a movement of the head) when the user exceeds the first threshold distance YT1 at time 2. A person of ordinary skill in the art should appreciate, in conjunction with a review of this disclosure, that the processor 150 can be programmed in any number of ways to provide a control signal to the user interface to provide a particular indication to the user in view of a particular lack of compliance with any number of possible predefined threshold values.

Figure 5:
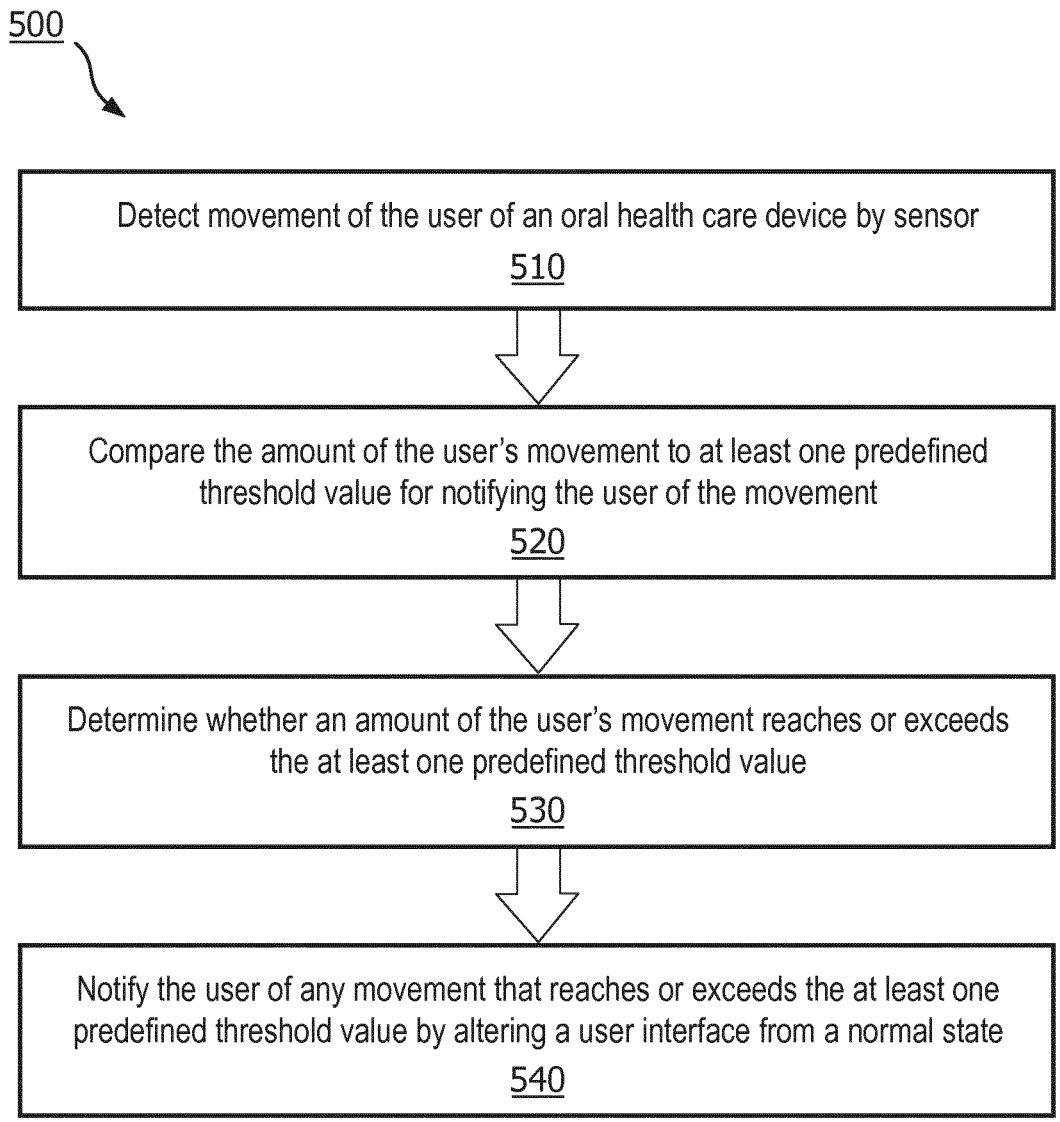
FIG. 5 is a flowchart of a method for detecting the movement of a user during use of an oral health care device and providing feedback to the user when the user's movement reaches or exceeds a threshold value according to an embodiment.

Referring to FIG. 5, a flow chart illustrating a method 500 for detecting the movement of a user during use of an oral health care device and providing feedback to the user when the user's movement reaches or exceeds a threshold value is disclosed. This method can be performed by either sensor 112 or 112' related embodiment, e.g., located outside of or embedded within the oral health care device 102 (or by the embodiments in combination), as described above. In step 510, movement of the user of an oral health care device is detected by sensor 112/112' and this information is transmitted to controller 142. In step 520, the amount of the user's movement is compared by the controller 142/processor 150 to at least one predefined threshold value for notifying the user of the movement. In step 530, a determination is made by the controller 142/processor 150 regarding whether an amount of the user's movement reaches or exceeds the at least one predefined threshold value. This step can include the steps of extracting by the controller 142/processor 150 (within any camera or non-camera sensor, as discussed herein and as should be understood by those of ordinary skill in the art in conjunction with a review of this disclosure) sets of visual features including positions of facial components of the user from the captured images or other obtained sensor data, calculating differences between the sets of visual features, and comparing the differences to predefined/threshold values. The differences between the sets of visual features can be distances between the positions of the facial components of the user from image to image, and the corresponding predefined values can be acceptable movement distances for each facial component. More generally, this step can include extracting by the controller 142/processor 150 sets of linear or non-linear features from the obtained sensor data, calculating by the controller 142/processor 150 differences between the sets of linear or non-linear features, and comparing the differences to predefined values. This step can also include calculating a weighted distance between the differences and corresponding predefined values. In step 540, the controller 142/processor 150 sends a signal to the user interface 114 to notify the user of any movement that reaches or exceeds the at least one predefined threshold value by altering a user interface from a normal state. Altering the user interface from a normal state can include blurring a visual image.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for providing feedback to a user of an oral health care device, the method comprising:
   detecting movement of a head of the user during use of the oral health care device relative to a reference point at a first point in time;
   determining an average movement of the head of the user over a period of time based in part on the detected movement of the head of the user from the reference point;
   determining whether the average movement of the head of the user reaches or exceeds a threshold value for notifying the user of the movement; and
   in an event the average movement reaches or exceeds the threshold value, notifying the user by altering a user interface associated with the oral health care device to provide a visual indication to the user, wherein the visual indication is related to a positioning of the user's head relative to the oral health care device over the period of time.

2. The method of claim 1, wherein the step of detecting movement of the head of the user includes capturing 2D or 3D images.

3. The method of claim 1, wherein the step of detecting movement of the head of the user includes using an accelerometer or a gyroscope positioned within the oral health care device.

4. The method of claim 1, wherein the step of detecting movement of the head of the user includes capturing images of the user using a camera.

5. The method of claim 4, wherein the step of determining whether the average movement reaches or exceeds the threshold value includes extracting sets of visual features including positions of facial components of the user from the captured images, calculating differences between the sets of visual features, and comparing the differences to predefined values.

6. The method of claim 1, wherein the step of determining whether the average movement reaches or exceeds the threshold value includes extracting sets of linear or non-linear features from captured sensor data, calculating differences between the sets of linear or non-linear features, and comparing the differences to predefined values.

7. The method of claim 5, wherein the step of determining whether the average movement reaches or exceeds the threshold value includes calculating a weighted distance between the differences and the corresponding predefined values.

8. The method of claim 5, wherein the differences between the sets of visual features are distances between the positions of the facial components of the user from image to image, and wherein the corresponding predefined values are acceptable movement distances for each facial component.

9. The method of claim 1, wherein the user interface includes a visual image and wherein altering the user interface includes blurring the visual image for an amount of time until the average movement no longer reaches or exceeds the threshold value.

10. The method of claim 1, wherein the visual indication is related to the positioning of the user's head relative to the oral health care device improving or worsening over the period of time.

11. The method of claim 7, wherein the weighted distance can be based on a direction of movement toward or away from an axis of the user's head.

12. A system for providing feedback to a user of an oral health care device, the system comprising:
a processor in communication with one or more position sensors and configured to determine positions of the user's head during use of the oral health care device relative to a reference point at a first point in time, the processor being configured to:
calculate average differences between the determined positions over a period of time based in part on the determined positions of the user's head from the reference point and determine if the average differences reach or exceed a threshold value for notifying the user; and
operate a user interface to provide a visual indication to the user in an event the average differences between the determined positions reach or exceed the threshold value, wherein the visual indication is related to a positioning of the user's head relative to the oral health care device over the period of time.

13. The system of claim 12, wherein the one or more position sensors include a camera to capture images of the user, and wherein the processor is configured to extract sets of visual features including positions of facial components of a user from the captured images, calculate differences between the sets of visual features, and compare the differences to predefined values.

14. The system of claim 12, wherein the processor is configured to extract sets of linear or non-linear features from captured sensor data, calculate differences between the sets of linear or non-linear features, and compare the differences to predefined values.

15. The system of claim 12, wherein the one or more position sensors comprise an accelerometer or a gyroscope positioned within the oral health care device.

16. The system of claim 13, wherein the processor is configured to calculate a weighted distance between the differences and the corresponding predefined values, and wherein the differences between the sets of visual features are distances between the positions of the facial components of the user from image to image, and wherein the corresponding predefined values are acceptable movement distances for each facial component.

17. The system of claim 12, wherein the user interface includes a visual image and wherein the processor is configured to blur the visual image in an event the average differences between the determined positions exceed the threshold value for an amount of time until the average differences between the determined positions no longer reach or exceed the threshold value.

18. The system of claim 16, wherein the weighted distance can be based on a direction of movement toward or away from an axis of the user's head.

19. The system of claim 12, wherein the visual indication is related to the positioning of the user's head improving or worsening over the period of time.

20. The system of claim 12, wherein the one or more position sensors include at least two position sensors and the processor is configured to analyze sensor input from the at least two position sensors, wherein the sensor input is averaged or weighted based on positioning or angle information of the at least two position sensors.

* * * * *